(12) United States Patent
Fuchs et al.

(10) Patent No.: US 6,222,033 B1
(45) Date of Patent: Apr. 24, 2001

(54) METHOD FOR PRODUCING CYCLIC LACTAMS

(75) Inventors: Eberhard Fuchs, Frankenthal; Rolf Fischer, Heidelberg, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/403,655

(22) PCT Filed: Apr. 30, 1998

(86) PCT No.: PCT/EP98/02571

§ 371 Date: Oct. 25, 1999

§ 102(e) Date: Oct. 25, 1999

(87) PCT Pub. No.: WO98/50355

PCT Pub. Date: Nov. 12, 1998

(30) Foreign Application Priority Data

May 2, 1997 (DE) .............................. 197 18 706

(51) Int. Cl.$^7$ .............................. C07D 201/08
(52) U.S. Cl. .............................. 540/539
(58) Field of Search .............................. 540/539

(56) References Cited

U.S. PATENT DOCUMENTS

| | | | |
|---|---|---|---|
| 2,245,129 | 6/1941 | Greenwalt | 260/2 |
| 2,301,964 | 11/1942 | Martin | 260/239 |
| 3,485,821 | 12/1969 | Sheehan | 260/239 |
| 3,988,319 | 10/1976 | Mares | 260/293 |
| 4,568,736 | 2/1986 | Curatolo et al. | 528/313 |
| 4,625,023 | 11/1986 | Mares et al. | 540/539 |
| 4,628,085 | 12/1986 | Mares et al. | 540/539 |
| 5,136,051 | 8/1992 | Schuster et al. | 548/553 |
| 5,493,021 | * 2/1996 | Barratt et al. | 540/539 |
| 5,495,014 | * 2/1996 | Fuchs et al. | 540/538 |
| 5,495,016 | * 2/1996 | Achhammer et al. | 540/539 |
| 5,646,277 | * 7/1997 | Fuchs et al. | 540/539 |
| 5,693,793 | * 12/1997 | Ritz et al. | 540/539 |
| 5,874,575 | * 2/1999 | Fuchs et al. | 540/539 |

FOREIGN PATENT DOCUMENTS

| | | |
|---|---|---|
| 952442 | 11/1956 | (DE) . |
| 4443125 | 6/1996 | (DE) . |
| 271815 | 6/1986 | (EP) . |
| 376122 | 7/1990 | (EP) . |
| 529470 | 3/1993 | (EP) . |
| 209021 | 1/1997 | (EP) . |
| 2029540 | 10/1970 | (FR) . |
| WO95/14665 | 6/1995 | (WO) . |
| WO 96/22974 | * 8/1996 | (WO) . |
| WO 96/36601 | 11/1996 | (WO) . |

OTHER PUBLICATIONS

Mares et al. "Kinetics of Caprolactam Formation from 6–Aminocaprioc Acid, Ester, and Amide" Ind. Eng. Chem. Process Des. Dev., vol. 17, No. 1, (1978) pp. 9–16.

A. Blade–Font "Facile Synthesis of Y–, 6–, and ε–Lactams by Cyclodehudration of ω–Amino Acids on Alumina of Silica Gel" Tetranedron Letters vol. 21 (1980) pp. 2443–2446.

Chemie–Ing.–Techn. 45 Nr. 24 (1973) pp. 1509–1524.

* cited by examiner

*Primary Examiner*—Bruck Kifle
(74) *Attorney, Agent, or Firm*—Keil & Weinkauf

(57) ABSTRACT

The disclosure is a process for preparing cyclic lactams of the formula I:

$$\begin{array}{c} \text{(I)} \\ \overset{A}{\underset{\underset{R^1}{N}}{\bigcirc}} C=O \end{array}$$

where $R^1$ is hydrogen, alkyl, cycloalkyl or aryl, and

A is $C_3$–$C_{12}$-alkylene unsubstituted or substituted by 1, 2, 3, 4, 5 or 6 substituents selected independently of one another from the group consisting of alkyl, cycloalkyl and aryl, by conversion of an ω-aminocarbonitrile of the formula II:

$$HR^1N\text{—}A\text{—}CN \qquad (II)$$

where $R^1$ and A are each as defined above, in the presence of at least one catalyst, which comprises converting said nitrile II into an oligomer mixture, and treating with superheated steam.

20 Claims, No Drawings

METHOD FOR PRODUCING CYCLIC LACTAMS

DESCRIPTION

The present invention relates to a process for preparing cyclic lactams by converting an ω-aminocarbonitrile in the presence of at least one catalyst.

Cyclic lactams are widely used as starting materials for producing polyamides (nylons) by ring-opening addition polymerization. The most important lactam is ε-caprolactam, the cyclic amide of ε-aminocaproic acid, which is mainly used for producing nylon 6 (Perlon®). The most important way to produce ε-caprolactam is the cyclohexanone oxime route, whereby cyclohexanone is reacted with hydroxylamine to form the oxime which is then subjected to a Beckmann rearrangement to form ε-caprolactam. This classic production route is in need of improvement, since it requires more than one step and inevitably by-produces sulfates or other by-products.

More recent processes for preparing cyclic lactams therefore utilize ω-aminocarbonitriles as starting materials. 6-Aminocapronitrile, for example, is prepared by selective hydrogenation of one of the two nitrile groups of adiponitrile.

U.S. Pat. No. 4,628,085 describes the reaction of 6-aminocapronitrile with water in the gas phase over a specific acidic silica gel at 300° C. By diluting the substrate with water, ammonia and hydrogen/nitrogen, it is possible to obtain caprolactam with quantitative conversion and a selectivity above 95%, but over just 150 h the silica gel deactivates with a marked reduction in conversion and selectivity.

A similar gas-phase process is described in U.S. Pat. No. 4,625,023. Here a very dilute gas stream of 6-aminocapronitrile, adiponitrile, ammonia, water and carrier gas is passed over a silica gel and a copper/chromium/barium titanium oxide catalyst bed. The caprolactam selectivity is 91% from a conversion of 85%. Here too the catalyst is found to deactivate rapidly.

U.S. Pat. No. 2,245,129 describes the preparation of linear polyamides in a two-step process. The first step comprises heating a 50% strength aqueous solution of 6-aminocapronitrile at 220° C. for 20 h to obtain a low molecular weight intermediate, which is further polymerized in the second step after ammonia and excess water have been removed.

U.S. Pat. No. 2,301,964 describes the uncatalyzed conversion of aminocapronitrile in the form of an aqueous solution into caprolactam at 285° C. The yield is distinctly below 80% and in addition an unspecified residue is obtained.

FR-A-2 029 540 describes a process for cyclizing 6-aminocapronitrile to caprolactam using catalysts selected from metallic Zn or Cu powder or oxides, hydroxides, halides, or cyanides of rubidium, of lead, of mercury or of elements having an atomic number within the range from 21 to 30 or 39 to 48. The catalysts described are used as suspension catalysts in stirred batch autoclaves. Caprolactam is obtained in yields of up to 83%. However, complete removal of the catalysts from the desired caprolactam presents problems, since caprolactam is capable of forming compounds with the soluble constituents of the metals used, or very fine particles can be formed by mechanical stirring.

U.S. Pat. No. 3,485,821 describes the cyclization to caprolactam of 6-aminocaproic acid in aqueous solution at 150–350° C.

DE-A-952 442 discloses a process wherein 5-formylvaleric esters are reductively aminated in two steps to obtain caprolactam as well as aminocaproic esters.

U.S. Pat. No. 3,988,319 describes a process for cyclizing 6-aminocaproic acid in methanol or ethanol as solvent. However, to avoid secondary reactions of the 6-aminocaproic acid, the amino acid has to be dissolved so slowly that it is not present as a solid. This requires temperatures of about 170° C. Furthermore, the water content of the solution must not exceed 40%, since open-chain polymers are otherwise formed. The water of reaction has to be removed if the alcohol is to be re-used.

Ind. Eng. Chem. Process Des. Dev., 17 (1978) 9–16 states that the cyclization of 6-aminocaproic acid in water to caprolactam leads to significant oligomer quantities unless concentrations below 13% and temperatures of around 300° C. are used.

A. Blade-Font, Tetrahedron Lett., 21 (1980) 2443–2446, describes the cyclization of 6-aminocaproic acid as a suspension in toluene in the presence of aluminum oxide or silica gel by removal of the water of reaction. For full desorption of the caprolactam, the catalyst has to be washed with methylene chloride/methanol and the polymer has to be precipitated with diethyl ether. The caprolactam yield after 20 h is 82% over aluminum oxide and 75% over silica gel.

EP-A-271 815 describes the cyclization of 6-aminocaproic esters to caprolactam by dissolving the ester in an aromatic hydrocarbon, cyclizing at 100 to 320° C. and at the same time removing the eliminated alcohol.

EP-A-376,122 describes the cyclization of 6-aminocaproic esters to caprolactam by dissolving the ester in an aromatic hydrocarbon and cyclizing at 230 to 350° C. in the additional presence of water.

It is known to crack nylon 6 back to caprolactam. Under the action of acidic or basic catalysts at elevated temperature, the cracking frequently takes place under the action of water vapor, ie. in the low pressure range.

Chem. Ing. Techn. 45 (1973) 1510 describes the industrial implementation of a cracking process for nylon 6 waste using superheated steam and concentrating a caprolactam/water solution to recover the caprolactam.

In EP-A-209021, the cracking is carried out in a fluidized aluminum oxide bed.

In EP-A 529 470, potassium carbonate is used as nylon 6 cracking catalyst and the reaction is carried out at 250 to 320° C. with simultaneous distillative removal of the caprolactam under reduced pressure.

All these processes for cracking nylon 6 to obtain caprolactam are disadvantageous because of the need to remove large amounts of water, which is very energy-intensive, and catalysts such as phosphoric acids and the salts thereof, potassium carbonate or alkali metal oxides. In the case of the gas-phase reactions, the polymer is heated to temperatures which are generally within the range from 270 to 400° C. and cracked together with water in a fluidized bed reactor. By-product formation and deactivation due to adhesive clumping of the catalyst bed are the consequence.

U.S. Pat. No. 4,568,736 describes a process for preparing polyamides by reacting ω-aminonitriles with water in the presence of a phosphorus-containing catalyst, for example phosphoric acid, phosphorous acid, hypophosphorous acid, etc. The reaction is carried out in a two stage process wherein the first stage comprises maintaining the process at a temperature between 200 and 300° C. and an elevated pressure between about 14 and 56 bar to form a low molecular weight polyamide intermediate and the second stage comprises reducing the pressure to less than or equal to atmospheric pressure and at the same time raising the temperature to polymerize the low molecular weight polyamide intermediate further to form high molecular weight polyamides. In general, this second step is carried out under inert gas. The products thus obtained are generally still phosphorus-comprising. Their quality does not equal that of products prepared by polymerization of cyclic lactams.

WO 95/14665 describes a process for preparing cyclic lactams by reacting aminocarbonitriles with water in the liquid phase in a fixed-bed reactor in the presence of heterogeneous catalysts having no soluble constituents under the reaction conditions. The reaction takes place in water or in aqueous solvent mixtures. The reaction temperature is generally within the range from about 140 to 320° C. at elevated pressures within the range of up to 250 bar. The disadvantage of this process is the formation of undesirable by-products, such as oligomers which are uncrackable under the reaction conditions and 6-aminocaproamide. Furthermore, when alcoholic solvent mixtures are used, unwanted esters will form, for example ethyl 6-aminocaproate.

DE-A-44 43 125 describes a process for preparing caprolactam by heating 6-aminocapronitrile in the presence of heterogeneous catalysts and water under elevated pressure wherein a first step comprises reacting a mixture of nitrile, water and an alcohol in the presence of the catalyst to form a mixture I which, as well as the desired caprolactam, further comprises water, alcohol, 6-aminocaproic ester, ammonia and high boilers, such as 6-aminocaproamide and oligomers of caprolactam. This mixture is then subjected to a distillative workup to obtain an overhead fraction, caprolactam and a bottom product. For further processing, the overhead fraction can be returned to the first reaction stage. However, if desired, it can also be fed together with the bottom product into a further reactor, optionally again mixed with alcohol and/or water and/or 6-aminocapronitrile and then likewise reacted to form caprolactam and worked up by distillation. If desired, it is also possible for just the bottom product of the distillation to be returned to the first reactor or into a further reactor, optionally admixed with water and/or alcohol, reheated and again worked up to obtain caprolactam. If desired, the bottom product can also be admixed with just water and heated in a separate reactor without addition of a catalyst and then worked up to caprolactam. If desired, the bottom product admixed with water and a base can also be heated in a further reactor and likewise worked up to caprolactam. To obtain good conversion rates and yields by this process, it is necessary to recycle the overhead fraction and the bottom product from the distillation to obtain caprolactam or, if necessary, to work them up separately. In the first case, this necessitates longer reactor residence times to obtain a high conversion and in the second case additional capital expenses for the reactors are required. This makes the process economically disadvantageous compared with others. In addition, as with the process described above, the use of alcohols as solvents leads to an unwanted formation of 6-aminocaproic esters.

It is an object of the present invention to provide an improved process for preparing cyclic lactams from ω-aminocarbonitriles. More specifically, the above-described disadvantages which render the process uneconomical shall be avoided at least in part. In addition, the novel process measures shall ideally obviate long residence times in the reactor through recycling of a major proportion of the reaction batch or high capital expenses through workup of the reaction batch in separate reactors.

We have found that this object is achieved, surprisingly, when ω-aminocarbonitriles are first catalytically converted into oligomers and these are then cracked to cyclic lactams using superheated steam.

The present invention accordingly provides a process for preparing cyclic lactams of the formula I:

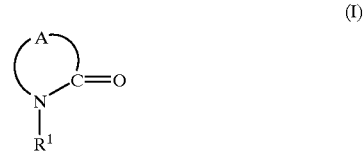

(I)

where $R^1$ is hydrogen, alkyl, cycloalkyl or aryl, and

A is $C_3$–$C_{12}$-alkylene unsubstituted or substituted by 1, 2, 3, 4, 5 or 6 substituents selected independently of one another from the group consisting of alkyl, cycloalkyl and aryl, by conversion of an ω-aminocarbonitrile of the formula II:

(II)

where $R^1$ and A are each as defined above, in the presence of a catalyst, which comprises:

a) converting said nitrile II into an oligomer mixture, b) adding a catalyst K1 and treating said K1-comprising oligomer mixture with superheated steam.

For the purposes of the present invention, the term "alkyl" comprehends straight-chain and branched alkyl groups. Alkyl is preferably straight-chain or branched $C_1$–$C_{12}$-alkyl and especially $C_1$–$C_6$-alkyl. Examples of alkyl groups include in particular methyl, ethyl, propyl, 1-methylethyl, butyl, 1-methylpropyl, 2-methylpropyl, 1,1-dimethylethyl, n-pentyl, n-hexyl, n-heptyl, octyl, nonyl, decyl and dodecyl.

Cycloalkyl is preferably $C_3$–$C_8$-cycloalkyl, such as cyclopropyl, cyclobutyl, cyclopentyl, cyclohexyl, cycloheptyl or cyclooctyl, or cyclopentylmethyl, cyclopentylethyl and cyclohexylmethyl and cyclohexylethyl.

Aryl is preferably phenyl, tolyl or naphthyl.

If 6-aminocapronitrile is used as the ω-aminocarbonitrile of the formula II, then oligomers include, for example, compounds of the formula:

where m is a whole number from 0 to 20,

X is CN, COOR, $CONH_2$ or COOH,

R is $C_1$–$C_5$-alkyl, or compounds of the formula

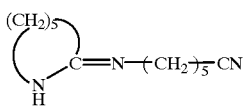

(caprolactamiminopentyl nitrile).

The oligomer mixture may further comprise residues of 6-aminocapronitrile and/or other precursors of caprolactam, for example 6-aminocaproic acid, esters and amides.

The novel process for preparing the cyclic lactams I is preferably carried out continuously, although the cracking can also be effected batchwise or semibatchwise. Suitable reactors will be known to those skilled in the art and generally include tubular reactors and heatable stirred reactors which, for process step b), are equipped with an apparatus to feed or introduce superheated steam and optionally with a distillation column. Suitable reaction vessels are described in Ullmann's Enzyklopädie der Technischen Chemie, 3rd edition, Volume 1, page 743 et seq. Suitable reaction vessels for working under superatmospheric pressure are found ibid., page 769 et seq. Suitable distillation columns are described ibid., page 429 et seq. To avoid any condensation at the top of the column when distillation is used in the production of higher boiling cyclic lactams, it is preferable to use a thermostatable column head. If desired, step a) and/or b) and/or a subsequent removal of the water can also be carried out in separate reactors.

Step a)

A first embodiment of the process according to the invention comprises converting the nitrile II into an oligomer mixture in water in the liquid phase. The temperatures generally range from about 100 to 350° C., preferably from about 120 to 250° C. The reaction time generally ranges from about 1 to 48 hours, preferably from about 2 to 24 hours.

The molar ratio of water to ω-aminocarbonitrile is generally within the range from about 0.01:1 to 20:1, preferably within the range from about 0.5:1 to 10:1.

In this variant, the ω-aminocarbonitrile of the formula II is advantageously used in water without a solvent. This avoids the prior art problem of forming the corresponding ω-aminocarboxylic esters. However, if desired, it is also possible to use solvent mixtures comprising water and an inert solvent. Suitable solvents include, for example, aliphatic hydrocarbons, such as petroleum ether, aromatic hydrocarbons, such as benzene, toluene and xylene, lactams, such as pyrrolidone, alkyl-substituted lactams, such as N-methylpyrrolidone, N-methylcaprolactam or N-ethylcaprolactam, and also carboxylic esters, preferably of carboxylic acids having from 1 to 8 carbon atoms.

Preferably, the ω-aminocarbonitriles act as both reactant and solvent.

In the first version of reaction step a), a catalyst K1 is present in the conversion of the nitrile II into the oligomer mixture. Suitable catalysts K1, which catalyze both the formation and the cracking of oligomers, are described hereinafter. In general, if a catalyst K1 is used in step a), there is no need for a further addition in step b).

The oligomer mixtures obtained in this first version a) of the process of the invention can generally be used in reaction step b) without further isolation or workup. The ammonia which is released in the course of the oligomerization can be separated off during the reaction of remain in the system.

In a second version of the process, oligomer mixtures can be prepared by the process described in U.S. Pat. No. 2,245,129, incorporated herein by reference. The further polymerization of the resulting oligomers which is described there is omitted. Instead, these oligomers are used for cracking in step b) of the process according to the invention.

In a third version of step a), the nitrile II is converted into an oligomer mixture in an inert solvent and in the absence of water. In this case, the reaction temperature is generally within the range from about 100 to 250° C.; preferably within the range from about 120 to 230° C. The reaction time is generally within the range from about 1 to 80 hours, preferably within the range from about 2 to 60 hours.

In an advantageous embodiment of this third version of reaction step a), the conversion of nitrile II into the oligomer mixture is effected in the presence of a catalyst K2. This catalyst K2 generally differs from the catalyst K1 used in step b). Suitable catalysts K2 are described hereinafter. When the reaction has ended, said catalyst K2 is separated from the resulting oligomer mixture, which for a heterogeneous catalyst is effected by customary methods, for example sedimenting, filtration or centrifugation. Suitable methods and apparatus for carrying out same are described in Ullmann's Enzyklopädie der Technischen Chemie, 3rd edition, Volume 1, page 470 et seq.

In a fourth version of reaction step a), oligomer mixtures are prepared using low valency ruthenium complexes as described by S.-I. Murahashi in Chemtracts: Inorg. Chem. 8 (1996), 89–105, or by copper catalysis according to customary processes known to one skilled in the art.

Prior to the further processing of the oligomer mixture in step b), it is generally customary to remove the added inert solvent and/or unconverted nitrile II and/or further volatile by-products from the mixture as well. This can be done, for example, by distillation, preferably under reduced pressure, for example at from about 1 to 100 mbar, at temperatures within the region of the previously selected reaction temperature, for example by means of the distillation column needed for step b).

Suitable inert solvents for preparing the oligomer mixtures in the second version of a) include the inert solvents previously mentioned in connection with the first version of the process.

After catalyst K2 and/or further volatiles have been removed, the oligomer mixture is used for cracking in step b), similarly to an oligomer mixture obtained by the first version of the process.

Step b)

According to the invention, the cyclic lactams of the formula I are obtained by treating the oligomer mixtures with superheated steam in the presence of a catalyst K1 to crack and also, if appropriate, to fractionate the oligomer mixtures. To this end, a catalyst K1 is added to the oligomer mixture, unless already present from step a). The superheated steam for the treatment is generally introduced into the reaction vessel together with the oligomer mixture. This can be accomplished, for example, via dip tubes underneath the liquid surface of the mixture. The temperature of the reaction mixture is generally within the range from about 200 to 350° C., preferably within the range from about 220 to 300° C. The temperature of the superheated steam is generally within the range from about 240 to 320° C., preferably within the range from about 260 to 300° C.

To avoid deposits of solid product in the column head in the case of higher boiling lactams, the column head can be of the thermostatable type, as mentioned above.

The steam throughput is generally within the range from about 200 to 800 g/l of batch hour, preferably within the range from about 400 to 600 g/l of batch hour.

The product comprises an aqueous mixture or aqueous fractions of lactams of the formula I, the level of I decreasing with increasing duration of the reaction or fractionation. The end of the cracking is discernible from a temperature decrease of the distillate at the top of the column. It is preferable to use only product-comprising fractions having a lactam content of more than 5% by weight, preferably more than 10% by weight, for the subsequent removal of water.

The bottom product of the fractionation in step b) can preferably be used for renewed cracking.

Following step b), water and any low boilers still present can be removed from the lactam fractions. The removal of water from the lactam fractions is effected by customary processes known to one skilled in the art. These include, for example, distillation at atmospheric or subatmospheric pressure. If the removal of low boilers gives rise to components which are suitable for use as monomeric building blocks, for example 6-aminocapronitrile or 6-aminocaproic esters, these can be recycled into step a) for oligomerization.

The process of the invention is preferably used to prepare cyclic lactams which are not N-substituted. In this case, $R^1$ is hydrogen in the formulae I and II. It is further preferable to use the process of the invention to prepare cyclic lactams of the formula I whose alkylene radical is not substituted. In this case, A is unsubstituted $C_3$–$C_{12}$-alkylene in the formulae I and II.

A is particularly preferably $C_3$-, $C_5$- or $C_{11}$-alkylene. The corresponding cyclic lactams of the formula I are γ-butyrolactam, ε-caprolactam and laurolactam.

The cyclic lactam of the formula I is particularly preferably ε-caprolactam.

In a preferred embodiment of the process according to the invention, catalyst K1 is a homogeneous catalyst. Preference is given to catalysts K1 of this type which comprise a phosphorus compound. Suitable catalysts include, for example, the polyamide production catalysts described in U.S. Pat. No. 4,568,736 which also catalyze the cracking of oligomeric amides. These include, for example, phosphoric acid, diphosphoric acid, metaphosphoric acid and polyphosphoric acids. Further suitable catalysts of this type include the salts and esters of phosphorous acid, such as trialkyl phosphites, eg. trimethyl phosphite and triethyl phosphite, and triaryl phosphites, eg. triphenyl phosphite. Further suitable catalysts K1 are phosphonic acid, its organic derivatives which have a phosphorus-carbon bond, for example alkylphosphonic acids and arylphosphonic acids, and also the esters and salts of phosphonic acid, the phosphonates, and the esters and salts of organic derivatives of phosphonic acid, the alkylphosphonates and arylphosphonates. Further suitable catalysts K1 are the esters and salts of phosphonous acid, the phosphonites. It is also possible to use phosphinic acid and its esters and salts, the phosphinates. The aforementioned catalysts K1 can be used alone or mixed.

In a preferred embodiment of the process according to the invention, catalyst K1 is orthophosphoric acid or a polyphosphoric acid.

The amount of catalyst K1 is generally within the range from about 0.01 to 10% by weight, preferably within the range from 0.1 to 3% by weight, based on the amount of ω-aminocarbonitrile of the formula II.

Catalyst K2 is preferably a heterogeneous catalyst.

Examples of usable heterogeneous catalysts K2 include acidic, basic or amphoteric oxides of the elements of the second, third or fourth main group of the periodic table, such as calcium oxide, magnesium oxide, boron oxide, aluminum oxide, tin oxide or silicon dioxide, such as fumed silica, silica gel, diatomite, quartz or mixtures thereof, also oxides of metals of the second, third, fourth, fifth or sixth transition group of the periodic table, such as zirconium oxide, zinc oxide or manganese oxide and preferably titanium oxide (amorphous, anatase or rutile), or mixtures thereof. It is also possible to use oxides of the lanthanides and actinides, such as cerium oxide, thorium oxide, praseodymium oxide, samarium oxide, rare earth mixed oxide or mixtures thereof with aforementioned oxides. Further catalysts include, for example, vanadium oxide, niobium oxide, iron oxide, chromium oxide, molybdenum oxide, tungsten oxide or mixtures thereof. Mixtures containing the oxides mentioned are likewise possible. Similarly, some sulfides, selenides and tellurides, such as zinc telluride, tin selenide, molybdenum sulfide, tungsten sulfide, sulfides of nickel, zinc and chromium are usable.

The aforementioned compounds can be doped with, or comprise, compounds of the 1st and 7th main groups of the periodic table.

It is further possible to use zeolites, phosphates and heteropolyacids and also acidic and alkaline ion exchangers such as Naphion® as suitable catalysts.

These catalysts may optionally comprise up to 50% by weight of copper, tin, zinc, manganese, iron, cobalt, nickel, ruthenium, palladium, platinum, silver or rhodium.

The catalysts K2 can be used as solid catalysts or as supported catalysts, depending on the composition of the catalyst. For instance, titanium dioxide can be used in the form of extrudates or as a thin layer of titanium dioxide applied to a support. To apply $TiO_2$ to a support such as silicon dioxide, aluminum oxide or zirconium dioxide, any method described in the literature can be used. Thus, a thin layer of $TiO_2$ can be applied by hydrolysis of organotitaniums such as titanium isopropoxide or titanium butoxide or by hydrolysis of $TiCl_4$ or other inorganic Ti-containing compounds. Sols comprising titanium oxide are likewise usable.

The amount of catalyst K2 is generally within the range from about 0.01 to 5% by weight, preferably within the range from about 0.1 to 3% by weight, based on the amount of ω-aminocarbonitrile.

The Examples which follow illustrate the invention.

EXAMPLES

Example 1

In a 500 ml three-neck flask equipped with a 15 cm glass tube vacuum column without packing, an inlet tube for steam and an electric thermometer, 250 g (2.2 mol) of 6-aminocapronitrile are mixed with 5 g of polyphosphoric acid (density 2.6 g/ml; 2% by weight, based on nitrile) dissolved in 20 g (1.1 mol) of water. The flask is heated by means of an 800 W reflector lamp. At the top of the column is a column head which is thermostated to 80° C. and features a water-cooled supercondenser. The cloudy solution is refluxed for 18 hours, during which the temperature rises from 133 to 155° C. The batch is then heated to 250° C. by means of the reflector lamp, 5 g of aminocapronitrile being removed as distillate. Thereafter, steam at 275° C. is introduced at 250° C. at a rate of 125 g/h, the superheated steam being superheated to the desired temperature under atmospheric pressure in an oil-heated coil (length 1500 mm; diameter 6 mm) and being passed into the reaction flask. The caprolactam-comprising steam passed through the hot reaction medium at 270–275° C. is condensed at 80° C. at the top of the column. The distillate is collected in varying fractions: 201 g of a 33.1% strength aqueous caprolactam solution are obtained after one hour. This fraction further comprises 30.4 g (0.27 mol) of caprolactamiminopentyl nitrile (caprolactim-(6-aminocapronitrile)) and a small amount of unconverted aminocapronitrile. After a further two hours, 315 g of an 18.7% strength caprolactam solution are taken off, followed two hours later by 277 g of a 14.4% strength caprolactam solution, by 94 g of an 8.7% strength caprolactam soslution after a further 45 minutes and 211 g of a now only 2.7% strength caprolactam solution after a further 1.5 hours. In total, 1099 g of a 15.8% strength (174 g of caprolactam) caprolactam solution are obtained in this way over 7.3 hours. The end of the cracking is discernible from a decreasing top-of-column temperature; the bottom product of 21.5 g comprises catalyst and residual oligomers and can be re-used for cracking.

The yield is 76% from a conversion of 87%. The selectivity is 87%. Re-using the bottom product portion increases the selectivity with respect to caprolactam.

Example 2

In an apparatus as described in Example 1, 1000 g of 6-aminocapronitrile in 500 g of o-xylene are refluxed with 100 g of titanium oxide at 160° C. for 40 hours. Thereafter, the solution is separated from the suspended titanium oxide and the solvent is distilled off and the residue is distilled at 1 mbar and 156–158° C. to obtain 600 g of pure caprolactamiminopentyl nitrile. The bottom product comprises 75 g of unconverted aminocapronitrile and 250 g of essentially crackable polymer.

In line with Example 1, 250 g of the caprolactamiminopentyl nitrile are admixed with 5 g of polyphosphoric acid (density 2.6 g/ml; 2% by weight, based on starting material) and the batch is heated to 250° C. by means of a reflector lamp. Steam at 275° C. is introduced at 250° C. at a rate of 125 g/h. The caprolactam-comprising steam passed through the hot reaction medium at 270–275° C. is condensed at 80° C. at the top of the column and the distillate is collected in varying fractions. 260 g of a 33.8% strength aqueous caprolactam solution are obtained after 1 hour. This fraction further comprises 78 g (0.7 mol) of caprolactamiminopentyl nitrile and traces of unconverted aminocapronitrile. After a further hour, 146 g of a 20.2% strength caprolactam solution are taken off, followed after a further 2 hours by 300 g of a 14.4% strength caprolactam solution and after another two hours by 258 g of a 7.9% strength caprolactam solution. In total, 964 g of an 18.8% strength (181 g of caprolactam) caprolactam solution are obtained in this way over 6 hours. The end of the cracking is discernible from a decreasing top-of-column temperature. The remaining bottom product proportion of 15.5% comprises catalyst and residual oligomers and can be re-used for cracking.

The yield is 67% from a conversion of 71%. The selectivity is 95%. Re-using the bottom product portion increases the selectivity with respect to caprolactam.

We claim:

1. A process for preparing cyclic lactams of the formula I:

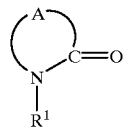

(I)

where $R^1$ is hydrogen, alkyl, cycloalkyl or aryl, and

A is $C_3$–$C_{12}$-alkylene, unsubstituted or substituted by 1, 2, 3, 4, 5 or 6 substituents selected independently of one another from the group consisting of alkyl, cycloalkyl and aryl, by conversion of an ω-aminocarbonitrile of the formula II:

(II)

where $R^1$ and A are each as defined above, in the presence of a homogeneous catalyst K1, which comprises a phosphorous compound, wherein K1 is selected from the group consisting of phosphoric acid, diphosphoric acid, metaphosphoric acid, polyphosphoric acid, the salts and esters of phosphorous acid, phosphonic acid, the salts, esters and organic derivatives of phosphonic acid, the esters and salts of organic derivatives of phosphonic acid, the esters and salts of phosphonous acid, phosphinic acid, the esters and salts of phosphinic acid, and mixtures thereof, the process comprises:

a) converting said nitrile II into an oligomer mixture, wherein step a) is effected in the presence of water and optionally in the presence of the catalyst K1 or wherein step a) is effected in an inert solvent and optionally in the presence of a heterogeneous catalyst K2 different from K1, wherein K2 is selected from the group consisting of oxides, sulfides, selenides and/or tellurides of elements of the $2^{nd}$, $3^{rd}$ or $4^{th}$ main group, of the $2^{nd}$, $3^{rd}$, $4^{th}$, $5^{th}$ or $6^{th}$ transition group, of the lanthanides, of the actinides, a zeolite, a phosphate, a heteropolyacid, an ion exchanger and mixtures thereof, and wherein said catalyst K2 is removed after converting said nitrile II into said oligomer mixture, b) adding a catalyst K1 unless already present from step a), and treating said K1-comprising oligomer mixture with superheated steam.

2. The process of claim 1, wherein said converting in step a) is effected at a temperature of from 100 to 350° C.

3. The process of claim 1, wherein said treating of said oligomer mixture in said step b) is effected at a temperature of from 200 to 350° C.

4. The process of claim 1, wherein said superheated steam is passed into said oligomer mixture in step b).

5. The process of claim 1, wherein said superheated steam is at a temperature of from 240 to 320° C.

6. The process of claim 1, wherein said catalyst K1 is selected from the group consisting of orthophosphoric acid, diphosphoric acid, metaphosphoric acid, polyphosphoric acids, trialkyl phosphites, triaryl phosphites, phosphonic acid, alkylphosphonic acids, arylphosphonic acids, phosphonates, alkylphosphonates, arylphosphonates, phosphonites, phosphinic acid, phosphinates and mixtures thereof.

7. The process of claim 1, wherein said catalyst K1 is orthophosphoric acid or a polyphosphoric acid.

8. The process of claim 1, wherein said catalyst K1 is used in an amount within the range from 0.01 to 10% by weight based on ω-aminocarbonitrile.

9. The process of claim 1, wherein said catalyst K2 further comprises at least one compound of the $1^{st}$ and/or $2^{nd}$ main group(s) of the periodic table.

10. The process of claim 1, wherein said catalyst K2 comprises at least one metal selected from the group consisting of Ti, Cu, Sn, Zn, Mn, Fe, Co, Ni, Ru, Pd, Pt, Ag and Rh.

11. The process of claim 1, wherein said catalyst K2 is used in an amount within the range from 0.01 to 5% by weight based on ω-aminocarbonitrile.

12. The process of claim 1, wherein $R^1$ is hydrogen in said formulae I and II.

13. The process of claim 1, wherein A is unsubstituted $C_3$–$C_{12}$-alkylene in said formulae I and II.

14. The process of claim 1, wherein said lactam of said formula I is ε-caprolactam.

15. The process of claim 8 wherein the range is from 0.1 to 3% by weight.

16. The process of claim 11 wherein the range is from 0.1 to 3% by weight.

17. The process of claim 1 wherein the homogeneous catalyst K1 is selected from the group consisting of diphosphoric acid, metaphosphoric acid, the salts and esters of phosphorous acid, phosphonic acid, the salts, esters and organic derivatives of phosphonic acid, the esters and salts of organic derivatives of phosphonic acid, the esters and salts of phosphonous acid, phosphinic acid, the esters and salts of phosphinic acid, and mixtures thereof.

18. The process of claim 1 wherein step a) is affected in water in the absence of an inert solvent.

19. The process of claim 1 wherein step a) is affected in the presence of water and catalyst K1.

20. The process of claim 1 wherein step a) is affected in an inert liquid in the absence of water.

* * * * *